Figure 1:
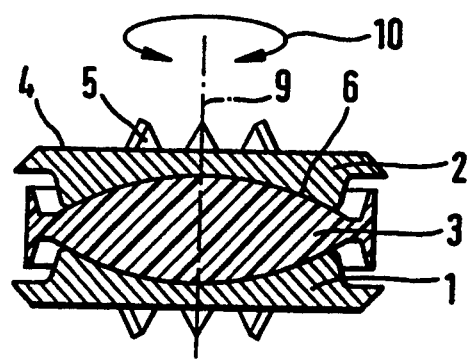

United States Patent [19]

Büttner-Janz et al.

[11] Patent Number: 5,401,269
[45] Date of Patent: Mar. 28, 1995

[54] INTERVERTEBRAL DISC ENDOPROSTHESIS

[75] Inventors: Karin Büttner-Janz, Berlin; Arnold Keller, Kayhude, both of Germany; Jean-Philippe Lemaire, Fontaine les Dijon, France

[73] Assignee: Waldemar Link GmbH & Co., Hamburg, Germany

[21] Appl. No.: 28,967

[22] Filed: Mar. 10, 1993

[30] Foreign Application Priority Data

Mar. 13, 1992 [DE] Germany .................. 42 08 116.5

[51] Int. Cl.⁶ .............................................. A61F 2/44
[52] U.S. Cl. ........................................ 623/17; 606/61
[58] Field of Search ............... 623/16, 18, 17; 606/61

[56] References Cited

U.S. PATENT DOCUMENTS

| | | | |
|---|---|---|---|
| 4,349,921 | 9/1982 | Kuntz | 623/17 |
| 4,759,766 | 7/1988 | Buettner-Janz et al. | 623/17 |
| 5,258,031 | 11/1993 | Salib et al. | 623/17 |

FOREIGN PATENT DOCUMENTS

| | | |
|---|---|---|
| 0317972A1 | 5/1989 | European Pat. Off. . |
| 3023353 | 4/1981 | Germany . |
| 3529761A1 | 7/1986 | Germany . |
| 239523A1 | 10/1986 | Germany . |

OTHER PUBLICATIONS

German Search Report for DE-P 42 08 116.5.
European Search report EP 93 10 2993.

*Primary Examiner*—David Isabella
*Attorney, Agent, or Firm*—Chilton, Alix & Van Kirk

[57] ABSTRACT

Intervertebral disc endoprosthesis with two prosthesis plates which are to be connected to the end plates of the relevant vertebrae, and with a prosthesis core which cooperates with at least one prosthesis plate via an articular surface permitting a rotational movement around the vertical axis, In order indeed to make possible a rotational movement around the vertical axis but to oppose this movement by a resistance, the articular surface forms curved arches of different average radius in the median section and in the frontal section. The radius of curvature in the sagittal section is expediently less than in the frontal section. To avoid excessive twisting it is possible to provide stops on the prosthesis plates and on the prosthesis core. These are designed, for example, as ribs and grooves which run in the median plane.

18 Claims, 4 Drawing Sheets

INTERVERTEBRAL DISC ENDOPROSTHESIS

The invention relates to an intervertebral disc endoprosthesis with two terminal plates which are to be connected to the endplates of the relevant vertebrae, and with a prosthesis core which cooperates with at least one terminal plate via an articular surface which permits a pivoting movement.

In known intervertebral disc endoprostheses of this type (EP-A 0 176 728, FR-A 2 659 226, DE-A 28 04 936), the articular surface is spherical. The vertebrae which are connected together by the prosthesis are therefore able freely to execute not only bending movements in the median plane and the frontal plane but also rotational movements around the vertical axis. This rotational movement is, moreover, not prevented by terminal plate parts striking one another. In another known intervertebral disc endoprosthesis (DE-C 30 23 353), by contrast, a rotational movement is made impossible by terminal plates striking one another; a pivoting movement is possible only in the median plane. This has the disadvantage not only that at the terminal plates parts made of the same material slide on one another with corresponding high abrasion and high friction, but also when there is a rotational movement of the body high forces act on the anchoring of the prosthesis to the relevant vertebrae and are disadvantageous with respect to permanent fixation of the prosthesis parts to the vertebrae. However, free rotary mobility of the above-mentioned prostheses also has disadvantages inasmuch as the necessary resistance to rotation which can be afforded by the natural intervertebral disc thanks to the structure and arrangement of its fibres is missing at least until sufficient scar tissue has formed, and therefore the vertebral arch joints may be overloaded, which may lead to problems. There is therefore a requirement for an intervertebral disc endoprosthesis which opposes twisting around the vertical axis by a resistance without this being achieved by striking against the terminal plates.

The solution according to the invention comprises the articular surface forming curved arches with a different average radius in the sagittal section and in the frontal section. The radii of curvature in the sagittal section are preferably smaller than in the frontal section. The radii of curvature in the principal directions which are at right angles to one another expediently differ by a factor of 1.2 to 2.5, preferably 1.5 to 2. They are expediently circular arches or approximate to the shape of a circular arch in the principal sectional planes.

The effect of this measure is that although rotation of the prosthesis parts around the vertical axis is possible, in this case the prosthesis is spread apart, as a consequence of the sliding of the lateral inclined flanks of the sliding surfaces on one another, which results in a restoring movement because of the loading weight. Conversely, it might also be said that the rotational movement of the prosthesis around the vertical axis is gently braked and the prosthesis has a tendency to return to the neutral position.

It may in some cases, despite the resistance which is generated according to the invention to rotation of the prosthesis around the vertical axis, be expedient to limit the maximum available angle of rotation by stops which can act between the prosthesis plates or, better, between the prosthesis core and the prosthesis plates cooperating therewith via articular surfaces. These stops are arranged so that in general they do not function because the rotational resistance generated by the shaping, according to the invention, of the sliding surfaces suffices within the normal range of rotation. They are intended merely to rule out rotation of such an extent that this might cause damage to the vertebral system or to the prosthesis. The striking together of prosthesis parts is generally avoided because the forces which may arise on vigorous striking when the body is swung may endanger the connection between the prosthesis part and the bone. This danger does not exist in the present case because the swinging of the body has been sufficiently attenuated by the rotational resistance of the sliding surfaces before the stops are reached.

In a preferred embodiment, the stops are incorporated in the sliding surfaces of the prosthesis core and of the prosthesis plate(s) which cooperate therewith. The latter may expediently assume the form of a groove in one surface and of a spring in the other surface, the profile of which being chosen so that the required range of rotation is ensured just as much as adequate bending forwards and to both sides. It is true that it is known (US-C 4 759 766) to provide the prosthesis plates and the prosthesis core with cooperating projections and grooves. However, the shape thereof is not suitable for forming a stop against rotational movement; nor is this necessary because the articular surfaces are cylindrical and do not provide for the possibility of rotation.

In addition to or instead of the groove-spring connection it is also possible to limit the rotation by a preferably encircling collar on one of the two parts and by a rim cooperating therewith on the other part. Such cooperating collars and rims on the prosthesis core and the prosthesis plates are known per se (EP-A 0 176 728, FIGS. 1 to 3) in the case of prosthesis parts with circular limits in order to hold the parts together with respect to lateral relative movement. When the basic shape of the parts is oval, they are also able to limit the rotation thereof around the vertical axis.

Figure 2:
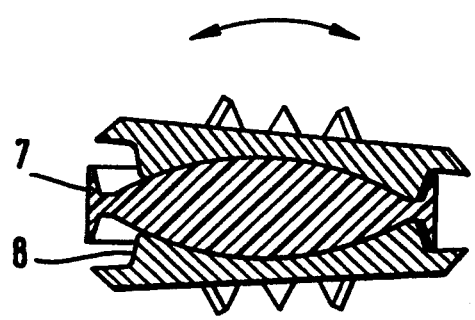
Figure 3:
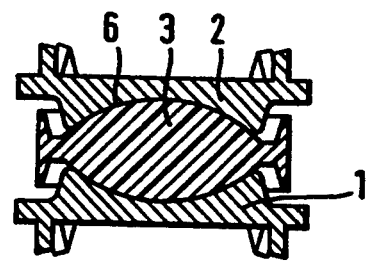
Figure 4:
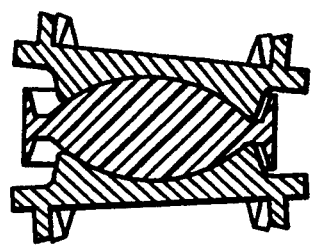
Figure 5:
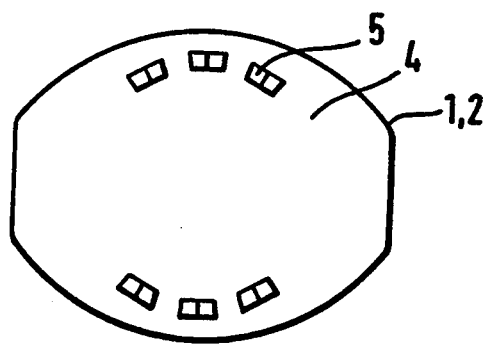
Figure 6:
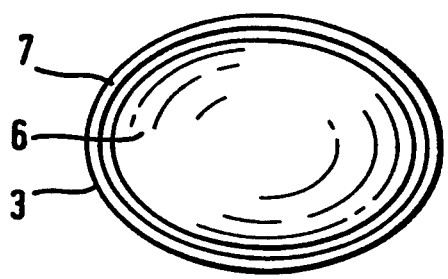
Figure 7:
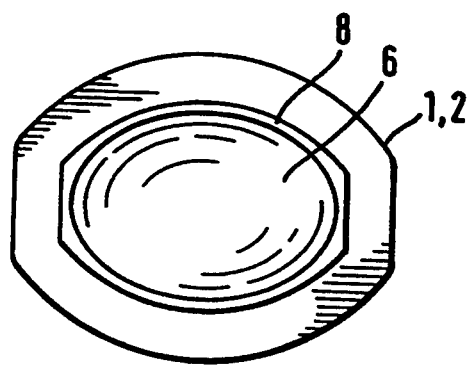
Figure 8:
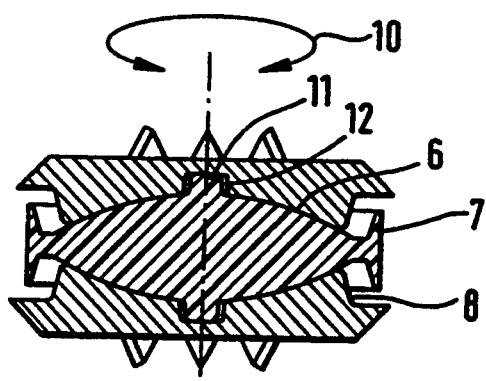
Figure 9:
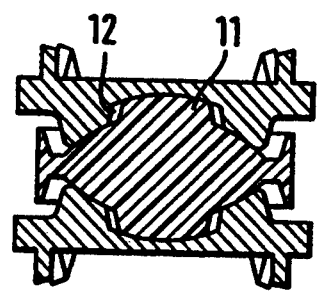
Figure 12:
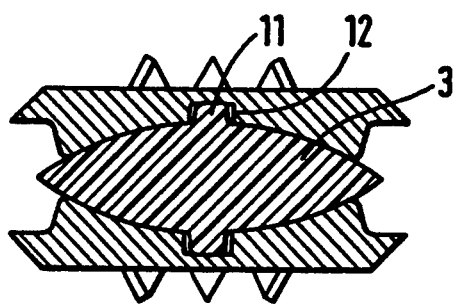
Figure 13:
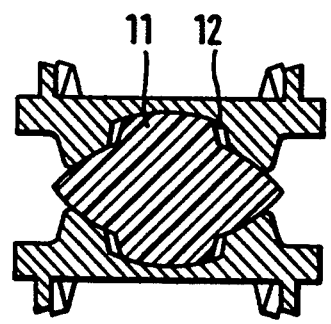
Figure 14:
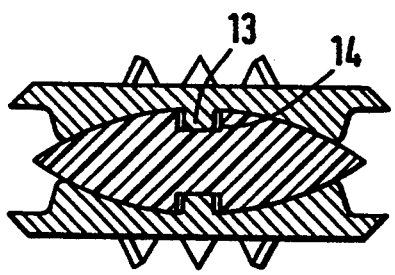
Figure 15:
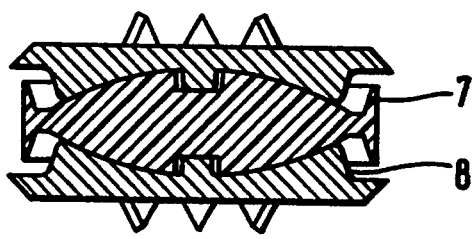

The invention is explained in detail hereinafter with reference to the drawing which illustrates advantageous exemplary embodiments. In this, FIG. 1 shows a central frontal section through the prosthesis in its neutral position, FIG. 2 shows a section corresponding to FIG. 1 on lateral bending, FIG. 3 shows a median section through the prosthesis, FIG. 4 shows a representation corresponding to FIG. 3 on bending forwards, FIG. 5 shows a top view of the outer surface of the prosthesis plates, FIG. 6 shows a top view of the prosthesis core, FIG. 7 shows a top view of the inside of the prosthesis plates, in each case of a first embodiment of the invention, FIGS. 8 to 11 show representations corresponding to FIGS. 1, 3, 6 and 7 of a second embodiment, FIGS. 12 and 13 show a representation corresponding to FIGS. 1 and 3 of a third embodiment, FIGS. 14 and 15 show two representations corresponding to FIG. 1 of a fourth and of a fifth embodiment of the invention.

The depicted intervertebral disc endoprosthesis consists of the prosthesis plates, namely the bottom plate 1 and the top plate 2, and of the prosthesis core 3. The prosthesis plates consist of metal. Their top surfaces 4, which are in contact with the vertebral top surfaces facing them are provided with teeth 5 which penetrate into the vertebrae and thus bring about fixation of the prosthesis with respect to the vertebrae.

The prosthesis core 3 consists of plastic with good sliding properties, especially high density polyethylene. The prosthesis plates and the prosthesis core form articular surfaces 6 which are congruent in the neutral state (FIGS. 1 and 3). In the central frontal section (FIG. 1) they represent circular arches just like in the median section (FIG. 3). In all the other sagittal and frontal sections they preferably form circular arches or approximate to circular arches. This results in the possibilities, which are illustrated in FIGS. 2 and 4, of a lateral and frontal bending movement, which may also occur in combination on oblique bending. The prosthesis core 3 is provided with a collar 7 which cooperates with the rim 8 of the prosthesis plates 1, 2 in order to limit the lateral relative movement of the prosthesis core with respect to the prosthesis plates, as is clearly evident in FIG. 2, right-hand side. To this extent, the prosthesis can be regarded as known.

According to the invention the radii of curvature of the articular surfaces 6 are different in the sagittal section and frontal section, namely smaller in the sagittal section (FIG. 3) than in the frontal section (FIG. 1). Whereas when the sliding surfaces have a spherical shape their congruence is retained even when the prosthesis plates are twisted around the vertical axis 9 with respect to the prosthesis core (in the direction of the arrow 10), the congruence is no longer present in the case of the articular surface configuration according to the invention in the sectional planes which differ from the principal planes. In these outer sectional planes, the prosthesis core rises on rotation at the flanks of the articular surfaces of the prosthesis plates. This results in the prosthesis plates being forced apart helically against the load of the body weight on them. As a consequence, the body weight causes a counteracting moment which attempts to rotate the prosthesis plates back into the neutral position. The twisting of the prosthesis plates acts against a resistance whose size is determined by the steepness of the cooperating flanks of the articular surfaces of the prosthesis plates and of the prosthesis core. The resistance can thus be dimensioned in a suitable way by the dimensioning of these flanks. It is expediently dimensioned so that in no case does it exceed the anchorage forces which can be transmitted between the prosthesis plates and the vertebrae.

At a certain angle of twisting, the collar 7 of the prosthesis core engages with the rim 8 of the prosthesis plates even when the axes of symmetry 9 of all the components are aligned with one another. This provides a stop against excessive twisting. It is equally possible to dimension the angle of twisting at which the stop function occurs by the dimensioning of the distance of the collar from the articular surfaces and from the rim 8 of the neutral position. It may be noted in this connection that the course of the collar 7 and of the rim 8 need not necessarily be parallel to the course of the outer limit of the articular surfaces 6.

The second embodiment shown in FIG. 8 to 11 agrees with the first embodiment unless described otherwise hereinafter.

In the case where the limit given by the collar 7 and the rim 8 to the rotational movement 10 is insufficient, the prosthesis core is provided with a rib 11 which runs in the median plane and which engages in a groove 12 which runs correspondingly in the assigned articular surface of the prosthesis plate(s). The outlines of the rib 11 and of the groove 12 in the top view (FIGS. 10 and 11) differ a little. Not only is the rib 11 a little shorter in the median section and in the frontal section than the width of the groove, so that the bending movement shown in FIGS. 2 and 4 can be carried out, but also, in particular, the rib 11 is narrower at its ends than in the central region and than the groove so that it is able to carry out a certain rotational movement within the groove 12. This rotational movement is terminated only when the narrower ends of the rib 11 strike against the side walls of the groove 12. If - as is assumed in the depicted examples - the prosthesis is provided with paired sliding surfaces above and below the prosthesis core, stops of the prosthesis core must, of course, be provided towards both prosthesis plates. If, on the other hand, the prosthesis core is firmly connected to a prosthesis plate, stops of this type on only one side suffice.

Since the rib 11 cooperates with the groove 12 to limit not only the rotational movement but also the bending movements of the prosthesis, the collar 7 on the prosthesis core is unnecessary, as is shown by the embodiment shown in FIGS. 12 and 13, which otherwise coincides with that shown in FIGS. 8 to 11.

Figure 10:
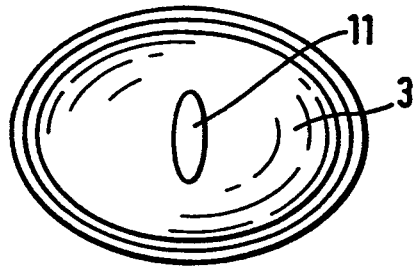
Figure 11:
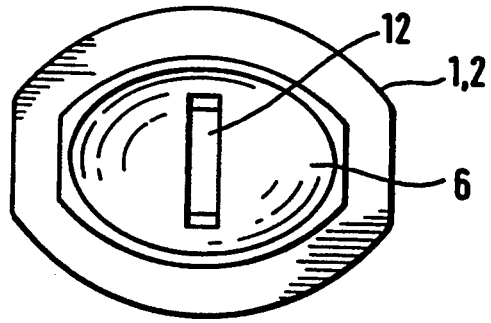

Whereas in the second and third embodiment (FIGS. 8 to 13) the rib was provided on the prosthesis core and the groove cooperating therewith was provided on the prosthesis plates, the positions are reversed in the embodiment shown in FIG. 14; the rib 13 on the prosthesis plates projects in each case into a groove 14 on the prosthesis core. In this case too, the rib 13 has the shape tapering towards the ends which is depicted in FIG. 10, whereas the groove 14 has parallel flanks.

The embodiment shown in FIG. 14 can be used without and with collar on the prosthesis core. Whereas the embodiment shown in FIG. 14 represents the version without collar, FIG. 15 illustrates the alternative with collar 7 on the prosthesis core 3.

We claim:

1. Intervertebral disc endoprosthesis comprising two prosthesis plates, which are to be inserted between two vertebrae, and a prosthesis core which cooperates with at least one prosthesis plate at an articular surface permitting a rotational movement around a vertical axis, wherein the articular surface has a median section and a frontal section, and forms in each section a curved arch having a radius of curvature that differs in one of said sections relative to the other of said sections.

2. Intervertebral disc endoprosthesis according to claim 1, wherein the radius of curvature in the curved arch of the median section is less than in the curved arch of the frontal section.

3. Intervertebral disc endoprosthesis according to claim 1, wherein the radius of curvature in the curved arch of one of said sections is a factor of 1.2 to 2.5 greater than in the other of said sections.

4. Intervertebral disc endoprosthesis according to claim 1, wherein the curved arches of both the median section and the frontal section are substantially circular.

5. Intervertebral disc endoprosthesis according to claim 1, wherein the prosthesis core and at least one of said plates cooperating therewith at an articular surface are provided with cooperating stops to limit relative pivoting movement.

6. Intervertebral disc endoprosthesis according to claim 5, wherein the prosthesis core and at least one of said plates are provided with at least one groove and a spring guided therein to provide for rotational play with respect to one another.

7. Intervertebral disc endoprosthesis according to claim 5, wherein one of the prosthesis core and the at least one prosthesis plate cooperating with the core has a collar and the other of said core and plate has a rim embraced by the collar.

8. Intervertebral disc endoprosthesis according to claim 1, wherein the prosthesis plates are provided with cooperating stops to limit pivoting movement.

9. An intervertebral disc endoprosthesis comprising a pair of prosthesis plates to be inserted between two vertebrae, at least one prosthesis plate having an articular surface, and a complementary surface functionally associated with the other prosthesis plate for cooperating with said articular surface to permit rotational movement around a vertical axis, the articular and complementary surfaces having complementary median and frontal sections forming curved arches having different radii of curvature in the median section and in the frontal section.

10. An intervertebral disc endoprosthesis according to claim 9, wherein the radius of curvature in the curved arch of the median section is less than the radius of curvature in the curved arch of the frontal section.

11. An intervertebral disc endoprosthesis according to claim 9, wherein the radius of curvature in the curved arch of one of said sections is a factor of 1.2 to 2.5 greater than in the other of said sections.

12. An intervertebral disc endoprosthesis according to claim 9, wherein the curved arches of the articular and complementary surfaces are substantially circular both in the median section and in the frontal section.

13. An intervertebral disc endoprosthesis according to claim 9, including stop means to limit relative pivotal movement between the prosthesis plates.

14. An intervertebral disc endoprosthesis according to claim 13, wherein the stop means includes an elongated groove in one of said articular and complementary surfaces and a rib in the other of said articular and complementary surfaces, said rib extending into said groove and being smaller than said groove to permit rotational play with respect to said groove.

15. An intervertebral disc endoprosthesis according to claim 9 including a core, wherein the complementary surface is formed on the core.

16. An intervertebral disc endoprosthesis according to claim 15, wherein one of the core and the prosthesis plate having an articular surface has a collar and the other of said core and said plate has a rim embraced by the collar with rotational play.

17. An intervertebral disc endoprosthesis according to claim 3, wherein the radii of curvature in the curved arches of the median and frontal sections differ with respect to each other by a multiple of 1.5 to 2.

18. An intervertebral disc endoprosthesis according to claim 11, wherein the radii of curvature in the curved arches of the median and frontal sections differ with respect to each other by a multiple of 1.5 to 2.

* * * * *